(12) United States Patent
Hara et al.

(10) Patent No.: US 7,661,820 B2
(45) Date of Patent: Feb. 16, 2010

(54) OPHTHALMOLOGIC INSTRUMENT

(75) Inventors: Naoko Hara, Nagoya (JP); Hisashi Kataoka, Nagoya (JP); Chihiro Kato, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 197 days.

(21) Appl. No.: 11/883,288

(22) PCT Filed: Jan. 18, 2006

(86) PCT No.: PCT/JP2006/300629

§ 371 (c)(1),
(2), (4) Date: Jul. 30, 2007

(87) PCT Pub. No.: WO2006/080217

PCT Pub. Date: Aug. 3, 2006

(65) Prior Publication Data

US 2008/0309872 A1    Dec. 18, 2008

(30) Foreign Application Priority Data

Jan. 31, 2005    (JP)    ............................. 2005-024135

(51) Int. Cl.
*A61B 3/14* (2006.01)
*A61B 3/10* (2006.01)
*A61B 3/00* (2006.01)

(52) U.S. Cl. .................. 351/206; 351/221; 351/246

(58) Field of Classification Search ......... 351/205–206, 351/210–212, 221, 246
See application file for complete search history.

(56) References Cited

U.S. PATENT DOCUMENTS 5,054,907 A * 10/1991 Sklar et al. .................. 351/212

| | | | |
|---|---|---|---|
| 6,299,305 B1 | 10/2001 | Miwa | |
| 2002/0180929 A1 | 12/2002 | Tseng | |
| 2004/0212781 A1 | 10/2004 | Mihashi et al. | |

FOREIGN PATENT DOCUMENTS

| EP | 1 029 504 A1 | 8/2000 |
|---|---|---|
| JP | 8-266469 A | 10/1996 |
| JP | 09 201334 | 8/1997 |
| JP | 2000-237135 A | 9/2000 |
| JP | 2000-254099 A | 9/2000 |
| JP | 2004-321508 A | 11/2004 |

\* cited by examiner

*Primary Examiner*—Scott J Sugarman
*Assistant Examiner*—Dawayne A Pinkney
(74) *Attorney, Agent, or Firm*—Muncy, Geissler, Olds & Lowe, PLLC

(57) ABSTRACT

The present invention provides an ophthalmologic apparatus that can noninvasively measure the state of the lacrimal layer formed on the cornea surface and that can quantitatively measure the state of the lacrimal layer without utilizing a reflection image from the retina.

The ophthalmologic apparatus according to the present invention comprises an optical projection system for projecting light of a specified pattern onto a cornea surface, and an imaging device for photographing a reflection image of the projected light from the cornea surface. An operating unit calculates the degree of distortion of the reflection image on the basis of the density value distribution of the image photographed by the imaging device. The operating unit can determine the state of the lacrimal layer using the calculated degree of distortion.

17 Claims, 10 Drawing Sheets

FIG. 8

|   | m→ |   |   |   |
|---|---|---|---|---|
| 0 | 0 | 1 | 2 | 3 |
| 0 | 1 | 2 | 3 | 3 |
| 1 | 2 | 2 | 3 | 3 |
| 2 | 2 | 3 | 3 | 2 |
| 2 | 3 | 3 | 2 | 2 | n↓

(a)

|   | 0 | 1 | 2 | 3 | i→ |
|---|---|---|---|---|---|
| 0 | 2 | 2 | 0 | 0 |   |
| 1 | 2 | 0 | 3 | 0 |   |
| 2 | 0 | 3 | 6 | 7 |   |
| 3 | 0 | 0 | 7 | 8 |   | j↓

(b)

(a)

(b)

OPHTHALMOLOGIC INSTRUMENT

TECHNICAL FIELD

The present invention relates to an ophthalmologic apparatus. More specifically, the present invention relates to an ophthalmologic apparatus that can evaluate the state of a lacrimal layer formed on a cornea surface.

BACKGROUND ART

A keratometer and a corneal topographer are known as ophthalmologic apparatuses for observing and measuring a cornea surface and the shape thereof. Generally these types of ophthalmologic apparatuses project light of a desired pattern onto the cornea surface. Then the state of the cornea surface, shape of the cornea, or other characteristic is measured by observing, photographing and analyzing a reflection image of the light pattern from the cornea surface.

The cornea surface is normally covered with a lacrimal fluid to form a lubricous fluid layer (lacrimal layer) on the cornea surface. The lacrimal layer gradually becomes thinner during the time the eyelid remains open after blinking and is eventually eliminated. When one's gaze is fixed on a monitor for an extended period, the number of blinks is reduced and the lacrimal layer is eliminated (a state of dryness referred to as dry eye). Moreover, due to individual differences in the rate in which the lacrimal layer is eliminated, there are people whose lacrimal layer reaches a state of dryness in a short period even without fixing their gaze on a monitor. People who experience this type of sudden dry eye daily often feel as if they have a foreign body in the cornea or the eyelid and thus often consult an eye specialist.

When eye specialists perform examinations on people whose chief complaint is dry eye, it is important to measure the state of the lacrimal layer formed on the cornea surface and to observe any changes over time. By studying the changes in the lacrimal layer over time from when the eyelid opens, the process by which the lacrimal layer is eliminated can be known. Thus ophthalmologic apparatuses are disclosed for measuring the state of the lacrimal layer formed on the cornea surface (for example, Japanese Laid-open Patent Publication No. 2000-237135, and Japanese Laid-open Patent Publication No. 2004-321508).

The ophthalmologic apparatus described in Japanese Laid-open Patent Publication No. 2000-237135 comprises an optical projection system and an optical receiving system. This ophthalmologic apparatus comprises a slit lamp microscope and a CCD camera for observing an eye to be examined. In this ophthalmologic apparatus a fluorescent dye is dropped onto the eye to be examined and the CCD camera is used to photograph the gray scale of the fluorescent reflection from the cornea surface. Then the region of dryness is identified by comparing the strength of the photographed fluorescent reflection with a predetermined threshold value. Lastly, the area of this identified region of dryness is displayed on a monitor. This ophthalmologic apparatus can quantitatively evaluate the state of dryness of the lacrimal layer, however, the inspection is invasive, as a fluorescent dye must be dropped onto the cornea.

Note that paragraph (0033) of Japanese Laid-open Patent Publication No. 2000-237135 describes an item which can measure a dry eye state without dropping a fluorescent dye onto the eye to be examined. More specifically, the document describes an item which can detect changes in the degree of dryness of a cornea surface over time by observing an interference pattern, in an image photographed with a halogen lamp as the only illumination, created by reflections from both the top and bottom surfaces of the lacrimal layer. However, it is not easy to uniformly illuminate the entire cornea surface and observe the interference pattern created by the reflections from both the top and bottom surfaces of the lacrimal layer, and thus the degree of dryness for the cornea surface cannot be detected with great precision. As a result, a fluorescent dye is indispensable for accurately performing an examination of the state of a dry eye.

In the ophthalmologic apparatus described in Japanese Laid-open Patent Publication No. 2004-321508, a beam of light is projected as appropriate onto the eye to be examined, and a CCD camera is used to photograph the reflection image from the cornea surface and the retina. Then the state of the lacrimal layer is quantitatively analyzed by using changes, due to the degree of dryness in the lacrimal layer, in the shape of the cornea, and wavefront aberrations. Thus the state of the lacrimal layer can be inspected noninvasively with this ophthalmologic apparatus. However, this ophthalmologic apparatus has various constraints that effect the measurement since a reflection from the retina is used. For example, when examining a patient with a cataract, light is scattered in the eyeball (varying with the severity of the cataract) causing interference with the reflected light beam observed by the CCD camera. Moreover, in principle, the diameter of the pupil constrains the range of measurement.

DISCLOSURE OF THE INVENTION

It is an object of the present invention to provide an ophthalmologic apparatus that can noninvasively measure the state of the lacrimal layer formed on the cornea surface and that can quantitatively measure the state of the lacrimal layer without utilizing a reflection image from the retina.

An ophthalmologic apparatus according to the present invention comprises a optical projection system for projecting light of a specified pattern onto a cornea surface, and an imaging device (for example, a CCD camera) for photographing a reflection image of the projected light from the cornea surface. This ophthalmologic apparatus further comprises an operating unit (a processor, microprocessor, controller or a similar object) for calculating the degree of distortion of the reflection image on the basis of the density value distribution of the image photographed by the imaging device, and for judging the state of the lacrimal layer using the calculated degree of distortion.

In this ophthalmologic apparatus, light of a specified pattern (for example, a ring-shaped pattern or a lattice-shaped pattern) is projected onto the cornea surface of the eye to be examined, and the reflection image (for example, a ring image or a lattice image) from the cornea surface is photographed. When the state of the lacrimal layer changes, the reflection image photographed by the imaging device also changes, and distortion arises in the photographed reflection image. This ophthalmologic apparatus judges the state of the lacrimal layer by using the distortion of the reflection image photographed by the imaging device. The distortion of the reflection image can be calculated on the basis of the density value distribution of the photographed reflection image from the cornea surface. This can be accomplished without the utilization of the reflection image from the retina.

Moreover, light of a specified pattern is projected onto the cornea surface of the eye to be examined, thus the photographed image includes a portion with a high density value (the portion onto which the light is projected) and a portion with a low density value (the portion onto which the light is not projected). Thus the distortion of the reflection image can be precisely calculated, and the state of the lacrimal layer can be quantitatively evaluated without utilizing a fluorescent dye.

The operating unit may calculate the degree of distortion of the reflection image from the relationship of the density values among pixels having a specified positional relationship in the photographed image. For example, if the degree of distortion of the reflection image is low when a light pattern having straight lines is projected onto the cornea surface, then the density value will be substantially uniform among pixels in the direction of this straight-line light pattern. On the other hand, when the degree of distortion of the reflection image is high, then the density value will not be uniform among pixels in the direction of this straight-line light pattern. Therefore, by evaluating the degree in which the density values among the pixels in the direction of this straight-line light pattern are uniform, the degree of distortion of the reflection image can be calculated.

Accordingly, by setting the above "specified positional relationship" in accordance with the pattern of light projected onto the cornea surface, and by calculating the relationship of the density values among the pixels having the "specified positional relationship", the degree of distortion of the reflection image can be calculated.

The operating unit may calculate a gray level co-occurrence matrix on the basis of the density value distribution of the photographed image, and calculate the degree of distortion from the calculated gray level co-occurrence matrix. By using the gray level co-occurrence matrix, the structural characteristics in the photographed image can be expressed, and the degree of distortion of the reflection image can be accurately calculated. When the gray level co-occurrence matrix is used, the degree of distortion is calculated using the contrast, uniformity of texture, gray scale correlation, or entropy.

The degree of distortion may also be calculated using a fractal dimension (an index indicating complexity) of the photographed image. The degree of distortion may also be calculated using a density histogram. Furthermore, the degree of distortion may be calculated by combining some of the above indexes (contrast, uniformity of texture, gray scale correlation, entropy, fractal dimension, density histogram).

Furthermore, the operating unit may calculate the degree of distortion of the reflection image using a method besides those described above. For example, the photographed image is binarized into pixels with a high density value (the portion that reflects the light pattern) and into pixels with a low density value (the portion that does not reflect the light pattern). Then the pattern structured by the high density values is thinned (by, for example, extracting the center lines), and the degree of distortion is calculated on the basis of the shape of the thinned pattern. For example, when a ring-shaped pattern is projected, thinning is performed on each ring, and the roundness of each ring is calculated. Then the calculated roundness values are set as the index (parameter) that indicates the degree of distortion.

Another option is to calculate the degree of straightness of each thinned line when the projected light has a lattice-shaped pattern, and to set these degrees of straightness as the index (parameter) that indicates the degree of distortion. A value for the degree of straightness can be calculated by integrating the absolute values of dy/dx (or dx/dy) in the x direction (or y direction) with each point on the thinned pattern plotted as an (x,y) coordinate.

Also the degree of distortion can be calculated from the number of points in which the thinned pattern is interrupted, since this pattern interruption arises when the change in the state of the lacrimal layer is extreme.

Moreover, points of light can be projected onto multiple locations on the cornea surface, and then the amount of change in the coordinates of the reflection image can be used as an index for the degree of distortion.

In the above ophthalmologic apparatus the operating unit may control the imaging device. In this case, the operating unit causes the imaging device to successively photograph the reflection image from the cornea surface at specified intervals of time. Then the operating unit calculates the degree of distortion for each photographed image. In the above case, the operating unit sets one of the photographed images as a reference. When the amount of change in the degree of distortion relative to the reference image exceeds the preset threshold value, the operating unit can determine that the lacrimal layer has reached a specified state (for example, a state in which a dry spot appears).

With such a structure, one of the images obtained through photography is set as a reference image, and then the state of the lacrimal layer is determined from the amount of change in the degree of distortion between the reference image and another image. By using the amount of change in the degree of distortion of the reflection image, the state of the lacrimal layer can be evaluated over time.

Moreover, by using the amount of change in the calculated degree of distortion, the following can be calculated: (1) the amount of time until breakup (until a dry spot appears), (2) the rate of the breakup, (3) the area of the breakup, (4) the ratio of the breakup, and other significant data. These indexes provide a comprehensive evaluation of the state of the dry eye.

Note that preferably the threshold value for determining whether the lacrimal layer has reached a specified state can be changed. Also, it is preferable that the change in the threshold value be input with an input device that can be operated by a person.

With such a structure the eye specialist can set an appropriate threshold value and perform an examination appropriate to the examinee.

In the above ophthalmologic apparatus, regions can also be set in the image photographed by the imaging device. Then the operating unit calculates the degree of distortion for each set region and determines the state of the lacrimal layer based on the amount of change in the degree of distortion for each set region.

With such a structure a position on the cornea surface and the state of the lacrimal layer at that position can be quantitatively evaluated. For example, it can be known whether a dry spot has occurred at any position on the cornea surface.

In the above ophthalmologic apparatus the operating unit preferably sets the first image photographed by the imaging device as the reference image and then continues to judge whether the lacrimal layer has reached a specified state by calculating, in the order of the photographed images, the amount of change in the degree of distortion. In this case the operating unit does not have to perform judgment on images photographed subsequent to the image for which it is determined that the lacrimal layer has reached a specified state.

With such a structure, an image photographed immediately after the blinking of the eye can be set as the reference image, thus the change over time in the lacrimal layer is accurately evaluated. Also, the state of the lacrimal layer can be efficiently evaluated since processing is not performed after it has been determined that the lacrimal layer has reached a specified state.

BRIEF DESCRIPTION OF THE DRAWINGS

FIG. 8 is a drawing for explaining a gray level co-occurrence matrix $P_\delta$ (i,j), with FIG. 8(a) showing a simplification of a region that is the object of image processing, and FIG. 8(b) showing the gray level co-occurrence matrix $P_\delta$ (i,j) calculated by setting $\delta=(1,0)$ for the image shown in FIG. 8(a).

FIG. 12 is a drawing for giving an explanation of a set region that is the object of image processing and that is set in the photographed image, in which FIG. 12(a) is an illustrative view of parting lines $L_1, L_2 \ldots$, set at an equal angular spacing in a circumferential direction from the center of image data, and rings $R_1, R_2 \ldots$, and FIG. 12(b) is an illustrative view of a set region $T_{ij}$ set in the vicinity of the intersection $P_{ij}$ of a parting line $L_i$ and a ring $R_j$.

BEST MODE FOR CARRYING OUT THE INVENTION

An explanation will be given below of an ophthalmologic apparatus (cornea topographer) according to one embodiment of the present invention.

Figure 1:
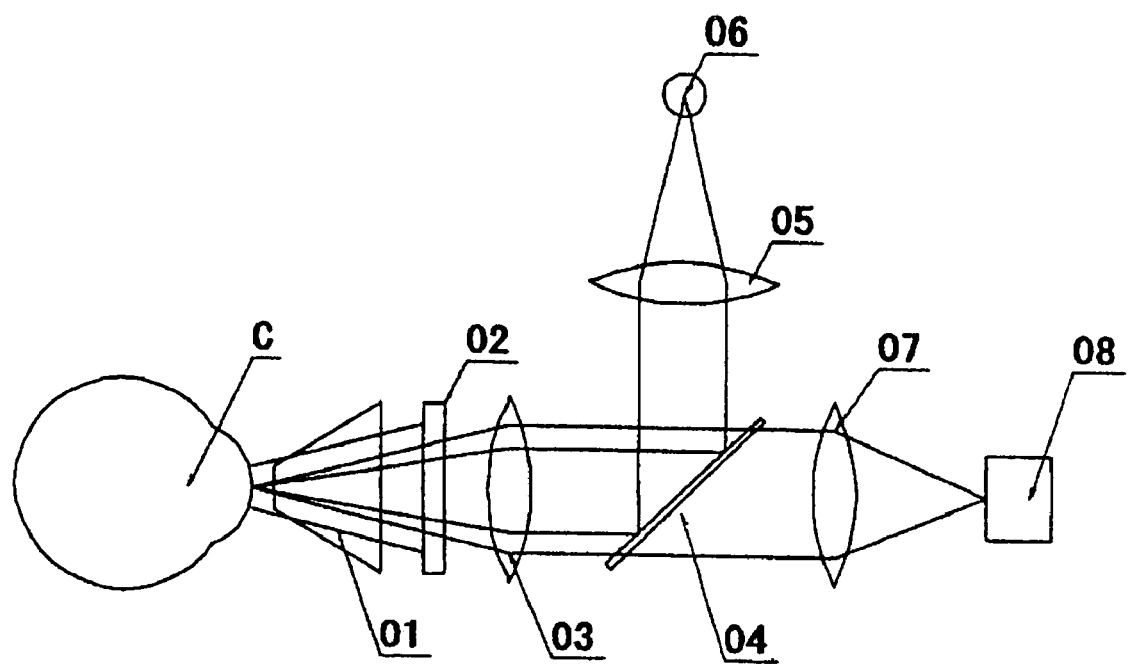
FIG. 1 is an illustrative view showing the complete structure of an optical system of an ophthalmologic apparatus according to the present embodiment.
Figure 2:
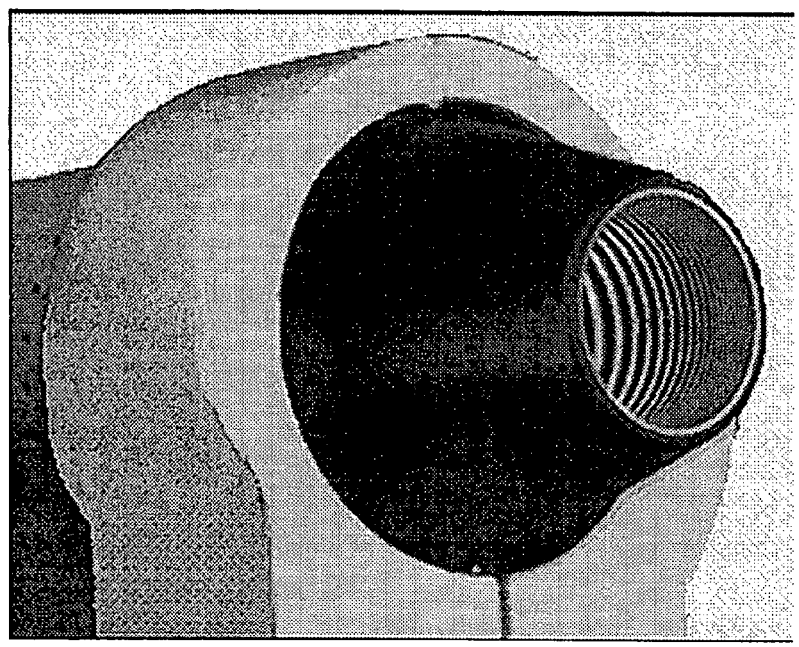
FIG. 2 is a perspective view of a cone disposed in the optical system shown in FIG. 1.
Figure 3:
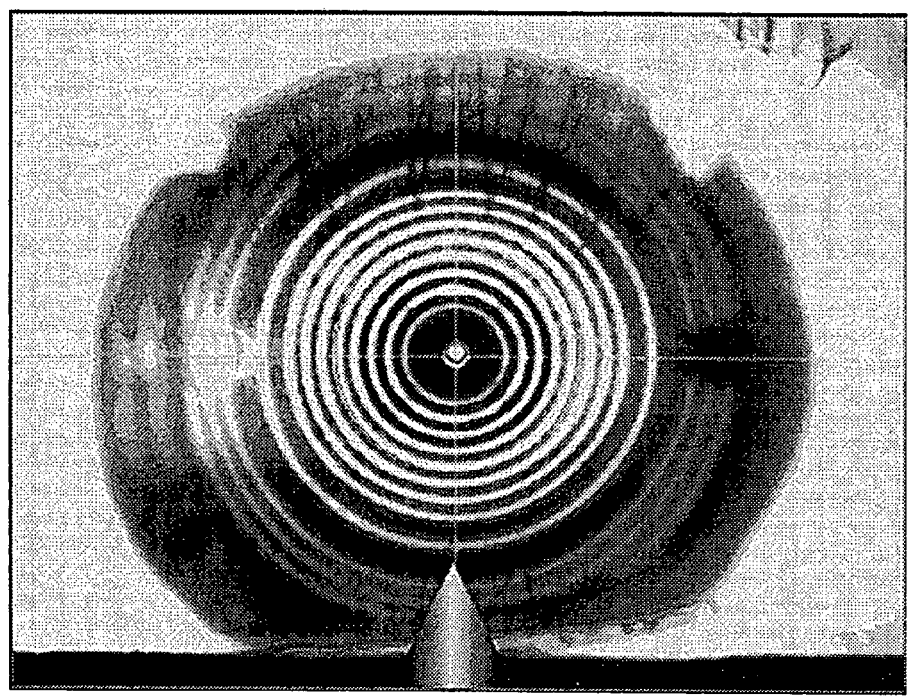
FIG. 3 is a view showing a projection pattern projected from the cone.

As shown in FIG. 1, the ophthalmologic apparatus of the present embodiment comprises a cone (01) which is disposed so as to face the cornea of an eye to be examined C, and an illumination device (02) (for example, an LED) disposed on the back surface of the cone (01). As shown in FIG. 2, the inner portion of the cone (01) is a hollow conical cylinder, and is formed from a transparent resin. A transparent film with a concentric circular pattern printed thereon is attached to the inner wall of the cone (01). The outer wall of the cone (01) has a coating applied that reflects light. Thus the illumination light from the illumination device (02) disposed on the back surface of the cone (01) is scattered inside the cone (01), and a portion of the light is blocked by the transparent film attached to the inner wall of the cone (01), and that portion of light is projected onto the cornea of the eye to be examined C. In this manner, a concentric circular light pattern as shown in FIG. 3 is projected onto the cornea of the eye to be examined. Note that as a method of projecting the desired pattern using the cone (01), a method can also be used in which the desired pattern is directly engraved into the inner wall of the cone (01), and then a coating with light blocking properties is applied to the engraved portion.

A lens (03) and a half mirror (04) are disposed on the back side of the illumination device (02). Light from a fixation-lamp point light source (06) falls on the half mirror (04) via a lens (05). The light from the fixation-lamp point light source (06) is reflected by the half mirror (04) and passes through the lens (03) to enter the cone (01). The cornea of the eye to be examined C is illuminated by light that enters the cone (01) from an opened center portion of the cone (01). As is shown in FIG. 3, the light from the fixation-lamp point light source (06) is adjusted to a position in the center of the concentric circular pattern formed by the cone (01). Also, light reflected from the cornea surface of the eye to be examined C (more specifically, light reflected from the concentric circular pattern of light and the light of the fixation lamp, which have been projected onto the cornea surface) passes through the cone (01), lens (03) and the half mirror (04) and is observed by a CCD camera (08) after focus adjustment is performed with a lens (07).

Note that in order to accurately measure the shape of the cornea with the above ophthalmologic apparatus, it is necessary to project a concentric ring pattern that is centered on the cornea vertex of the eye to be examined C. Thus when measuring the shape of the cornea, the fixation-lamp point light source (06) is turned on to make the examinee fix his/her gaze on the light. The examiner adjusts the position of the optical system relative to the eye to be examined C so that the light of the fixation-lamp point light source (06) observed by the CCD camera (08) is centered on the cornea of the eye to be examined C. In this manner, a concentric ring pattern is projected, centered on the cornea vertex of the eye to be examined C.

Figure 4:
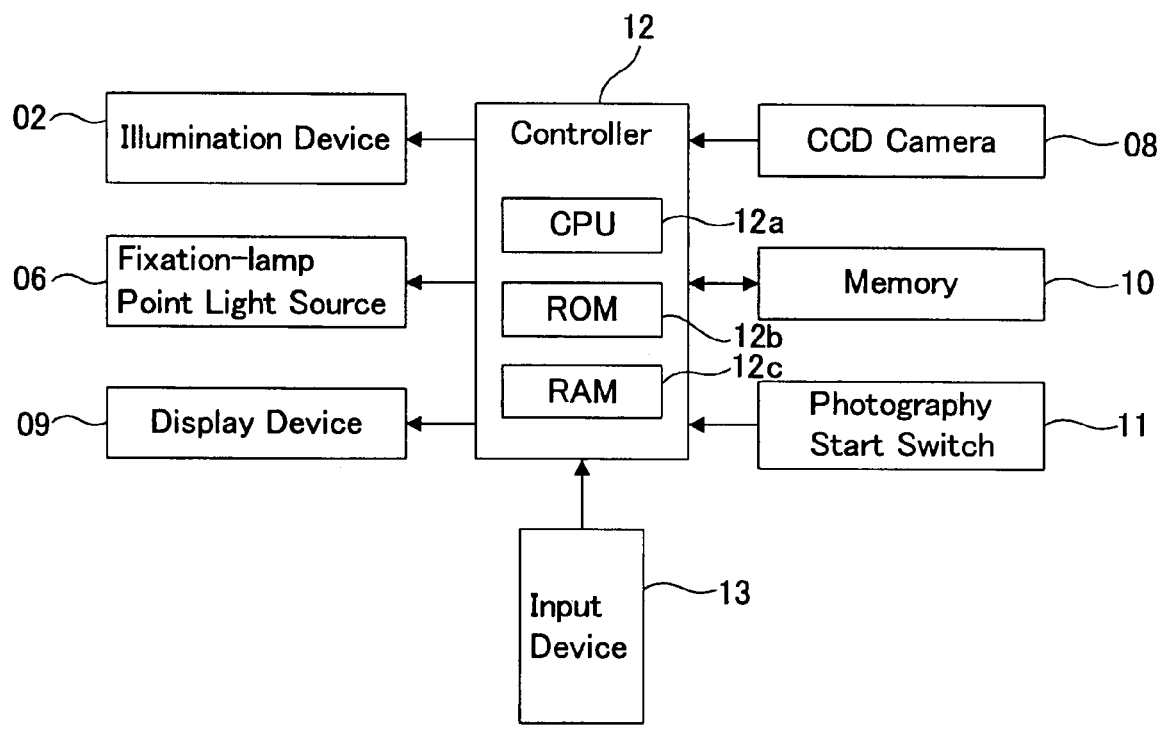
FIG. 4 is a block drawing showing the structure of a control system of the ophthalmologic apparatus shown in FIG. 1.

An explanation will be given of the structure of a control system for the above ophthalmologic apparatus. FIG. 4 shows the structure of the control system for the ophthalmologic apparatus according to the present embodiment. As shown in FIG. 4, control of the ophthalmologic apparatus is performed by a controller (12).

The controller (12) is structured by a computer that comprises a CPU 12a, ROM 12b, and RAM 12c. The CCD camera (08), a photography start switch (11), an input device (13) and memory (10) are connected to the controller 12. The photography start switch (11) and the input device (13) are operated by the examiner. When the examiner operates the photography start switch (11), the controller (12) activates a specified program, measures the amount of change over time in a lacrimal layer formed on the cornea surface, and determines whether there is a dry eye state. A threshold value (to be explained in detail below), for determining whether there is a dry eye state, can be changed using the input device (13). By changing the threshold value, measurement can be performed in a manner appropriate to the examinee. Note that image data photographed by the CCD camera (08) is input into the controller (12) and stored in the memory (10).

Also, the illumination device (02), the fixation-lamp point light source (06) and the display device (09) are connected to the controller 12. The controller (12) performs ON/OFF control on the illumination device (02) and the fixation-lamp point light source (06), and also displays images photographed by the CCD camera (08) on the display device (09).

Figure 5:
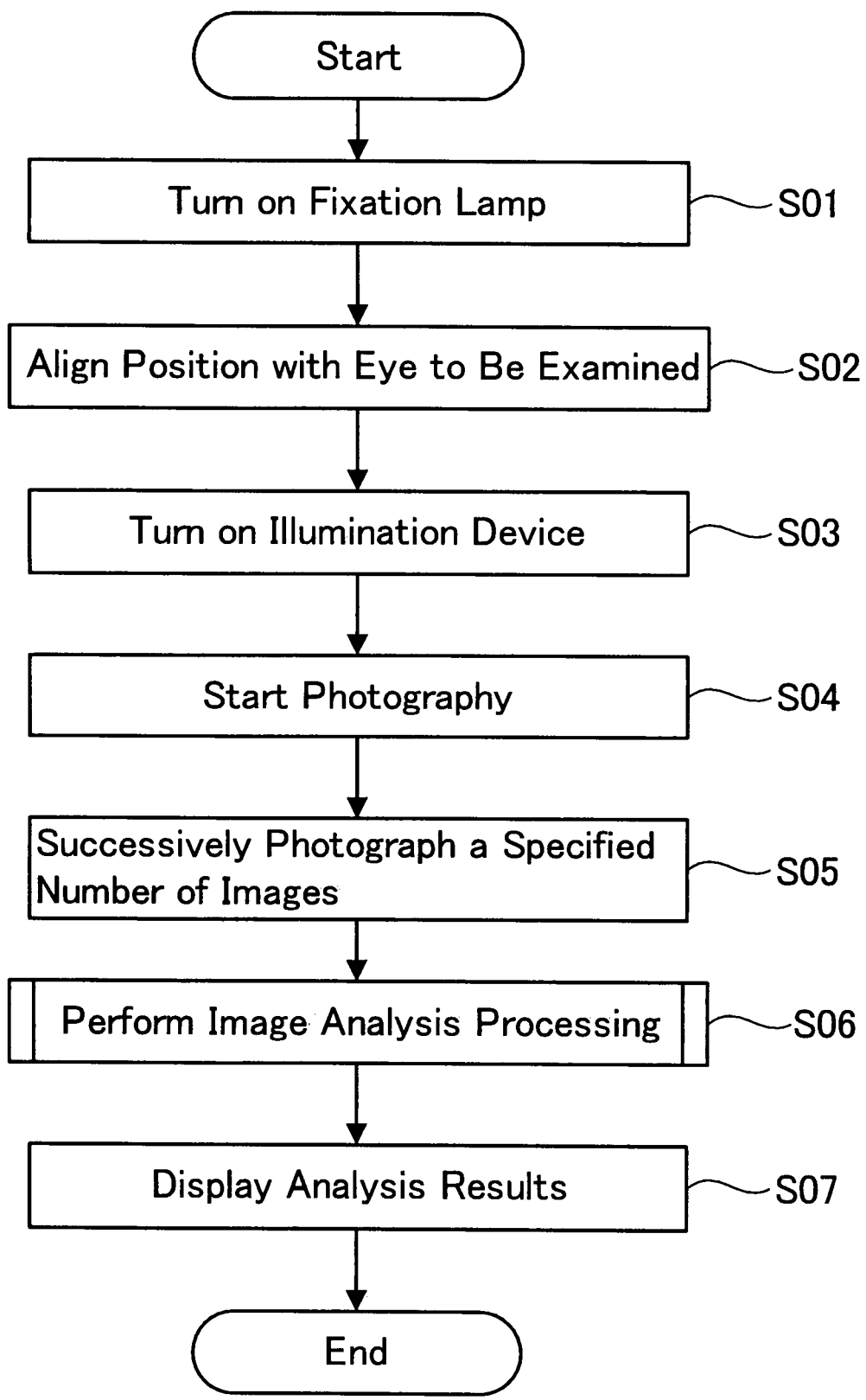
FIG. 5 is a flowchart for measuring change over time in a lacrimal layer formed on a cornea surface.

Next an explanation will be given of the procedures for using the above ophthalmologic apparatus to measure the change over time of the lacrimal layer formed on the cornea surface. FIG. 5 is a flow chart showing the measurement procedures.

As shown in FIG. 5, the examiner first turns on the fixation-lamp point light source (06) and instructs the examinee to fix his/her gaze on the fixation lamp (S01). When the fixation-lamp point light source (06) is turned on, an image photographed by the CCD camera (08) is displayed on the display device (09). The display device (09) displays the bright point formed by the fixation-lamp point light source (06), and an image of the cornea of the eye to be examined C. Note that turning on the fixation-lamp point light source (06) and the illumination device (02) may be performed simultaneously.

Next the examiner performs positional adjustment of the optical system for the eye to be examined C so that the front portion of the eye to be examined (09) is positioned on the center of the display screen (more specifically, so that the light reflected from the fixation-lamp point light source (06) is positioned on the center of the cornea C) (S02).

When positional adjustment of the optical system is finished, the illumination device (02) is turned on, and a concentric circular light pattern is projected onto the cornea surface of the eye to be examined C (S03). Next the examiner causes the examinee to momentarily close his or her eyelid to form a uniform lacrimal layer on the cornea surface, and then operates the photography start switch (11) at the same time the examinee opens his or her eyelid (S04).

Figure 6:
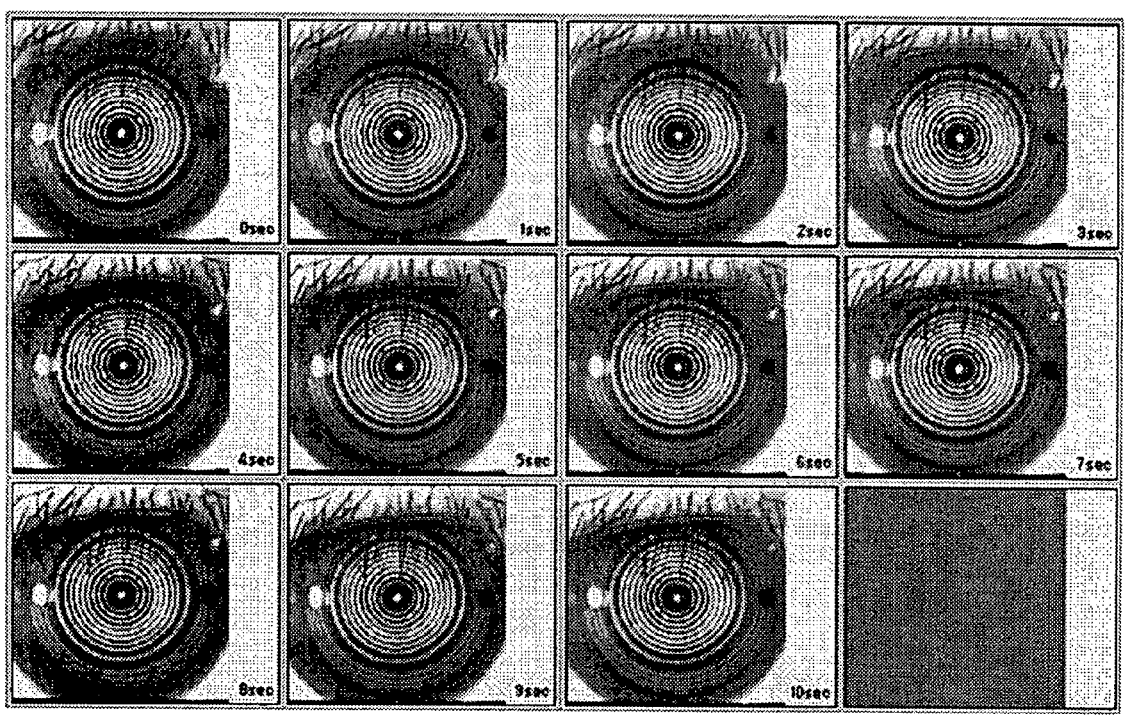
FIG. 6 is a drawing that displays in chronological order a series of images photographed through the measuring process of FIG. 5, the images being shown at time t=0, 1, 2, 3, 4, 5, 6, 7, 8, 9 and 10 seconds.

When the examiner operates the photography start switch (11), the controller (12) operates the CCD camera (08) and at specified time intervals, photographs only a specified number of images of the reflection pattern from the cornea surface (S05). In the present embodiment, the reflection pattern from the cornea surface is photographed every one second from the operation of the photography start switch (11) until ten seconds have passed. Accordingly, the processing of step S05 causes eleven cornea surface images to be photographed. The photographed series of images is stored in the memory (10) in chronological order. The series of images obtained through the processing of step S05 is shown in FIG. 6 in chronological order. Note that the examiner is to be instructed not to blink his or her eye until the photography processing in step S05 is completed.

Figure 7:
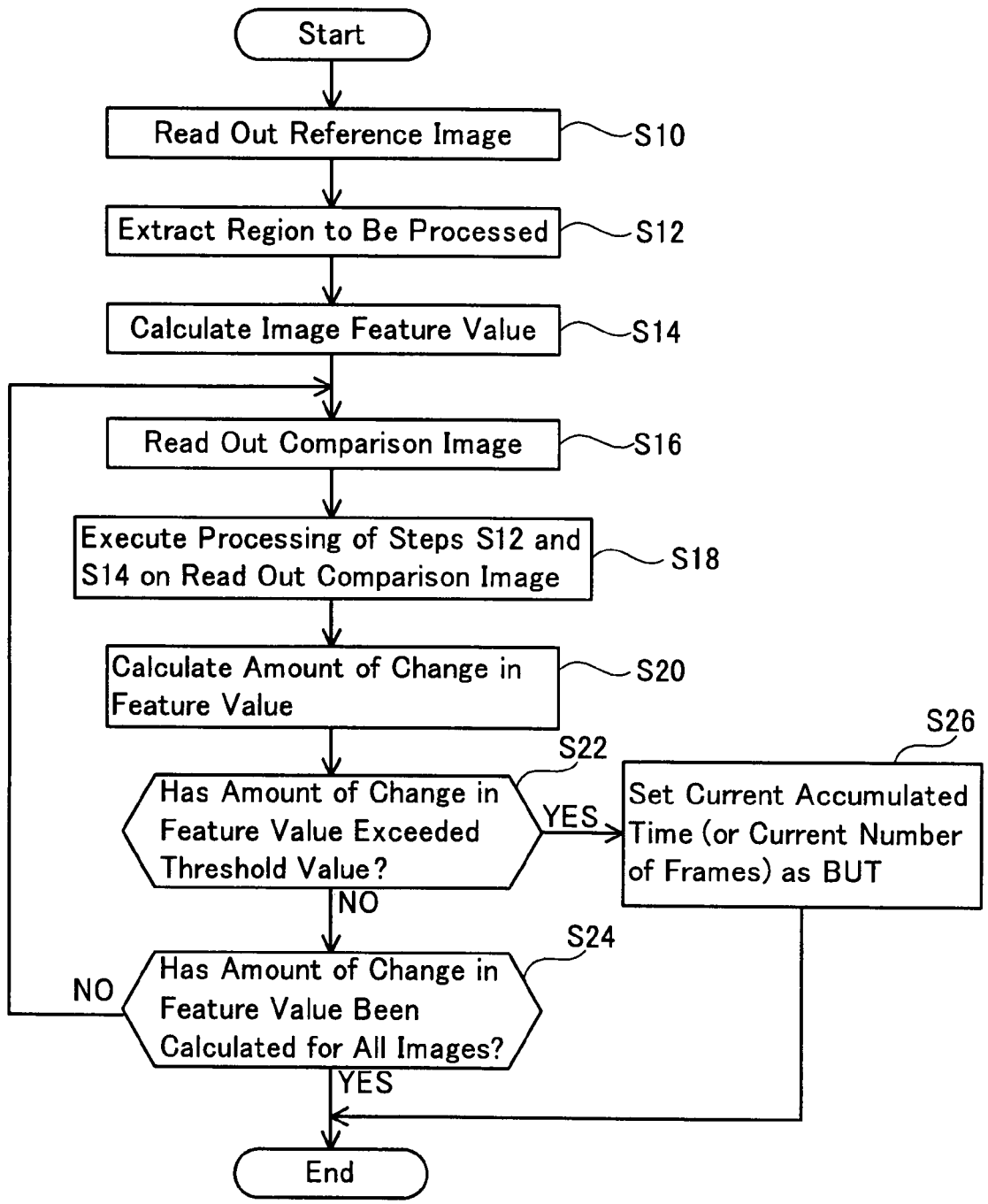
FIG. 7 is a flowchart showing the procedures of image analysis processing.

After the photography processing of step S05 is completed, the controller (12) begins image analysis processing of each image photographed in step S05 (S06). FIG. 7 is a flowchart showing the procedures of analysis processing of an image. As shown in FIG. 7, the controller (12) first reads out from the memory (10), as a reference image, an image (elapsed time t=0 seconds) photographed at the exact time the photography start switch (11) is operated (S10).

Figure 9:
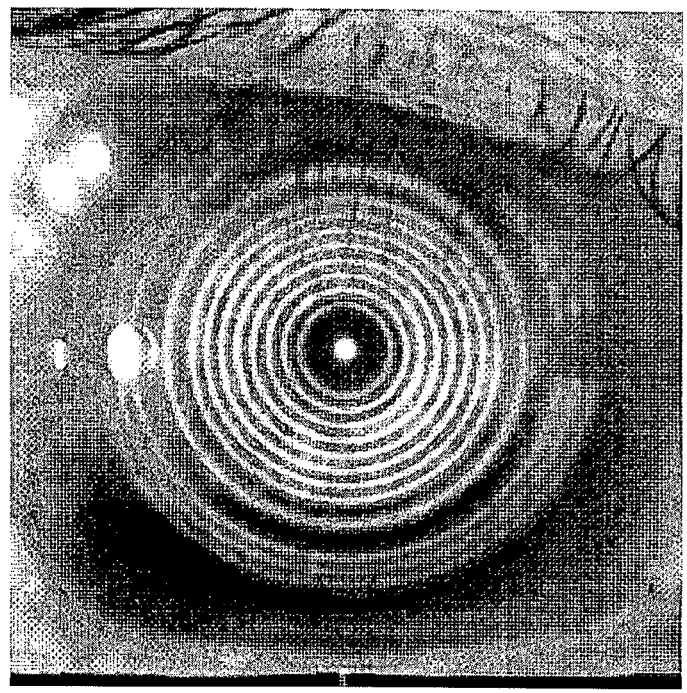
FIG. 9 is an actual photographed image (immediately after the eyelid opens (t=0)).
Figure 10:
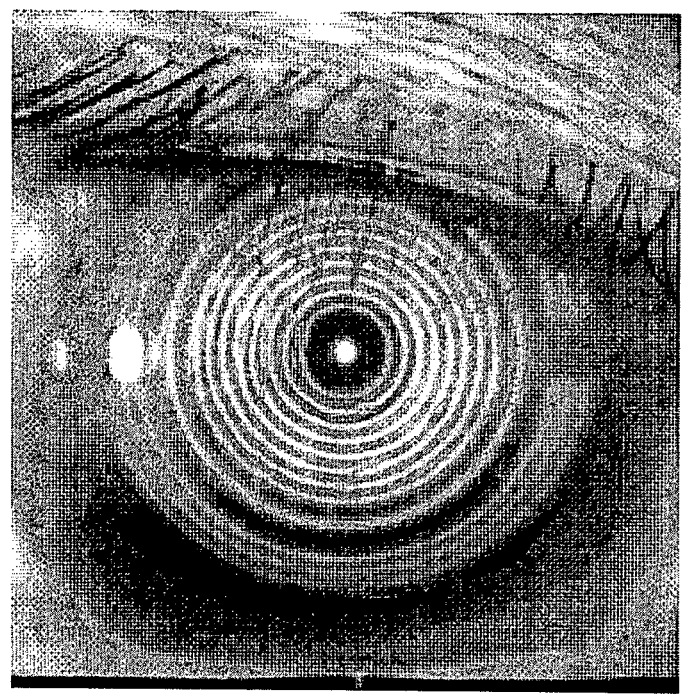
FIG. 10 is an actual photographed image (two seconds after the eyelid opens (t=2)).

Next, a region that is to be the object of image processing is extracted from the readout image data (S12). More specifically, as shown in FIGS. 9 and 10, not only the reflected light of the light pattern from the cornea surface, but also other elements are included in the image photographed by the CCD camera (08). Thus the processing in step S12 extracts only the region that is the object of image processing and shortens the image processing time. Note that the region that is the object of image processing is limited to only the region that is illuminated by the light pattern. As a result, the degree of distortion of the light pattern (referred to as image feature value below) can be calculated with favorable precision.

Figure 12:
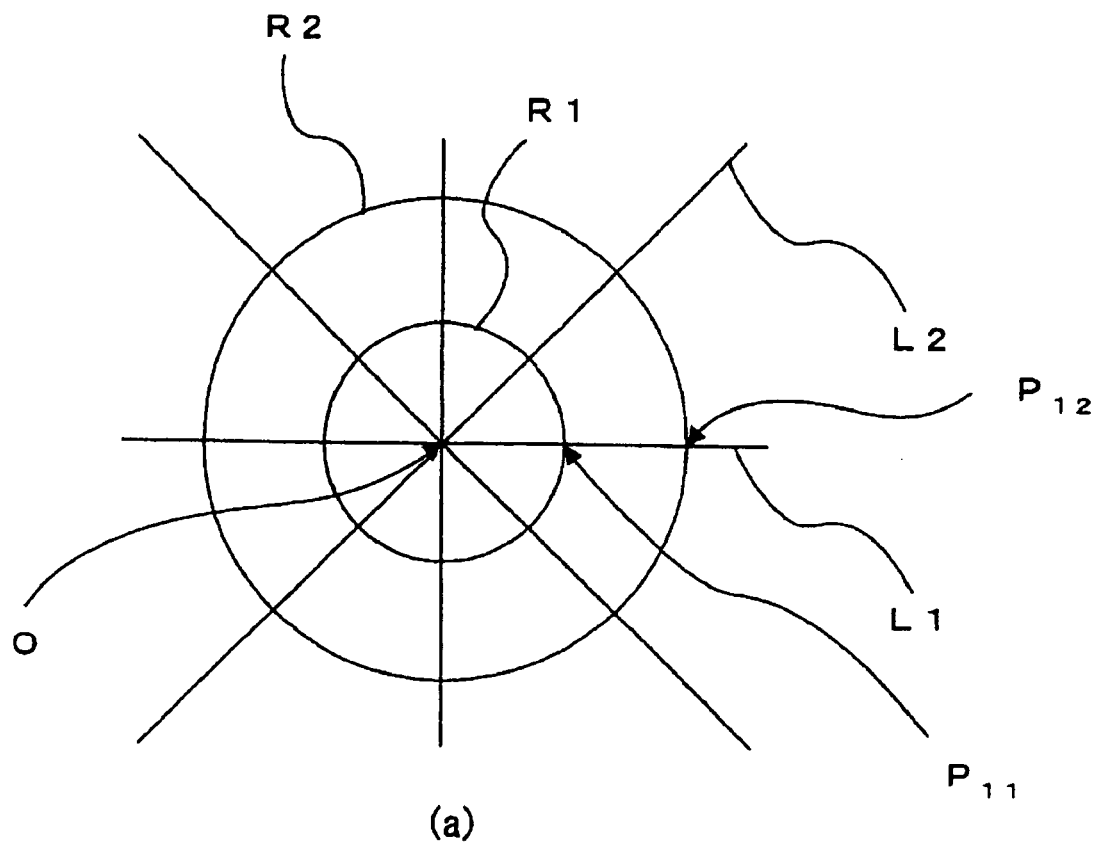
Figure 12:
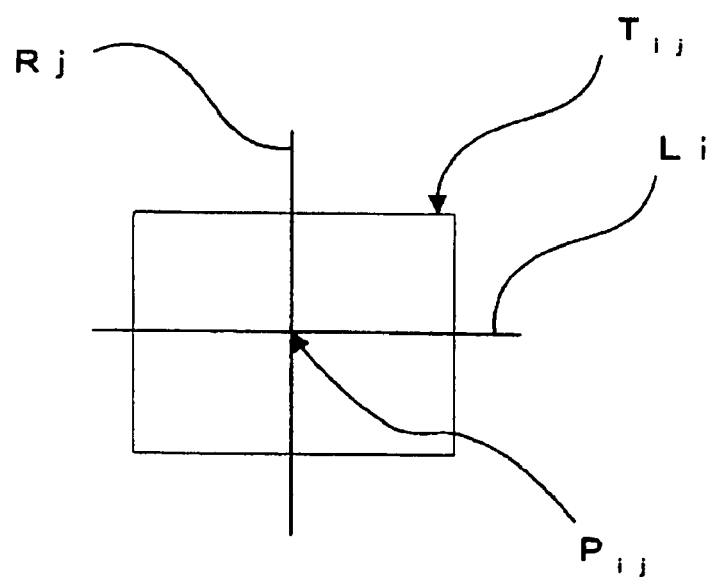

In the present embodiment, as shown in FIG. 12(a), parting lines $L_1$, $L_2$ . . . are set at an equal angular spacing in a circumferential direction from the center O (the center of the cornea C) of the image data, then the intersections $P_{11}$, $P_{12}$ . . . of the parting lines $L_1$, $L_2$ . . . and rings $R_1$, $R_2$ . . . are calculated. As shown in FIG. 12(b), a region $T_{ij}$ is set in the vicinity of an intersection $P_{ij}$, and this region $T_{ij}$ is set as the object of image processing. Accordingly, in the present embodiment, regions that are set as the objects of image processing are limited to the number (i×j) of intersections $P_{ij}$. Then the image feature values are calculated for each set region $T_{ij}$, and the changes over time in the lacrimal layer in these regions are evaluated.

Note that in the present embodiment, the regions that are the objects of image processing $T_{ij}$ are set by calculating the coordinates of each intersection $P_{ij}$ for only the reference image (at t=0 seconds). The coordinates for the intersection of parting line $L_i$ and ring $R_j$ are not calculated for the subsequent photographed images, but the image feature values for the set regions $T_{ij}$, which are the objects of image processing, are calculated.

When a region that is the object of image processing is extracted, the image feature value for that region is calculated (S14). In the present embodiment, the image feature value is calculated using a gray level co-occurrence matrix. $P_\delta$ (i,j). The gray level co-occurrence matrix is one that uses the frequencies of $P_\delta$ (i,j) as elements, in which j is the density of a point at a distance, from a point having a density i, that has a specified displacement $\delta=(\Delta m, \Delta n)$. A detailed explanation will be given with reference to FIG. 8.

FIG. 8(a) shows pixels having an order of (5×5) that simplify a region that is the object of image processing, and shows the density value for each pixel. Note that the density values for the pixels are classified into four ranges that are indicated by the numbers zero to three. For example, the pixel at coordinate (0,0) has a density value of "0" and the pixel at coordinate (2,2) has a density value of "2".

FIG. 8(b) shows the gray level co-occurrence matrix $P_\delta$ (i,j) calculated with $\delta=(1,0)$ for the image of FIG. 8(a). Since $\delta=(1,0)$, the gray level co-occurrence matrix $P_\delta$ (i,j) is formed from the calculations of the number of horizontally (in the m direction) adjacent pixel pairs that have a relationship of density values that are i and j. For example, the number of elements (i,j)=(2,1) enclosed by thick black lines in FIG. 8(b) is the number in FIG. 8(a) of pixels having a density value of "1" adjacent (in the horizontal direction) to pixels having a density value of "2", and this number is shown by the portions enclosed by thick black lines in FIG. 8(a). Thus $P_\delta$ (2,1)=3.

Note that the number of pixels having a density value of "1" adjacent (in the horizontal direction) to pixels having a density value of "2" is identical to the number of pixels having a density value of "2" adjacent (in the horizontal direction) to pixels having a density value of "1". Thus the gray level co-occurrence matrix $P_\delta$ (i,j) is symmetrical. Also, in the example shown in FIG. 8, the gray level co-occurrence matrix $P_\delta$ (i,j) is a 4×4 matrix since the density values of the pixels have four ranges.

As is clear from the above description, the gray level co-occurrence matrix $P_\delta$ (i,j) indicates the relationships of the density values of pixel pairs having a positional relationship set as $\delta=(\Delta m, \Delta n)$. Accordingly, by setting, $\delta$ (more specifically $\Delta m$, $\Delta n$) in accordance with the pattern of light projected onto the cornea surface, the image feature value (more specifically, the degree of distortion of the pattern image) can be calculated using the gray level co-occurrence matrix $P_\delta$ (i,j). In the present embodiment, $\delta$ is set in the direction of the light pattern for each region that is the object of image processing. More specifically, it is preferable to use $\delta$ so as to set the direction between the set pixels with consideration to the shape of the light pattern, and to use $\delta$ so as to set the distance between the set pixels with consideration to the resolution of the CCD camera (08).

When the gray level co-occurrence matrix $P_\delta(i,j)$ is calculated, the following gray level co-occurrence matrices $P_\delta(i,j)$ are used to calculate the image feature value. For example, the following can be used: (1) the contrast, (2) the uniformity of texture, (3) the gray scale correlation, (4) the entropy.

(1) Contrast

The contrast is greater in proportion to the number of pixels having a large difference in density values between pixel pairs that have a positional relationship set by $\delta=(\Delta m, \Delta n)$. Accordingly, when the positional relationship is set as $\delta=(\Delta m, \Delta n)$ in order to compare the density values of pixels pairs on the pattern, if there is no distortion of the pattern image the density values of the pixel pairs will be identical, thus the calculated contrast will be low. On the other hand, the contrast becomes gradually greater in accordance with a greater degree of distortion of the pattern images. Note that the contrast is calculated using the formula below.

$$\text{Contrast} = \sum_i \sum_j (i-j)^2 P_\delta(i, j) \qquad \text{[Formula 1]}$$

(2) Uniformity of Texture

The uniformity of texture increases when there are more specified pixel pairs (for example, pixel pairs with an identical density value). Accordingly, by setting $\delta=(\Delta m, \Delta n)$ as appropriate, the distortion of the pattern image can be indicated by the uniformity of texture. Note that the uniformity of texture can be calculated using the formula below.

$$\text{angular-second-moment} = \sum_i \sum_j \{P_\delta(i, j)\}^2 \qquad \text{[Formula 2]}$$

(3) Gray Scale Correlation

The gray scale correlation is an index showing directional strength, and its value is greater when a periodical pattern appears in a given direction. In the present embodiment, as shown in FIGS. 9 and 10, a light pattern is projected having ring shapes that have a substantially identical spacing. Thus when $\delta$ is set in a direction perpendicular to the ring pattern, if there is no distortion of the pattern image, a region with a high density value (the pixels onto which the light pattern is projected) and a region with a low density value (the pixels onto which the light pattern is not projected) periodically appear in that direction. Thus the degree of distortion of the pattern image can be indicated by the gray scale correlation. Note that the gray scale correlation can be calculated using the formula below. Here $\mu x$ and $\mu y$ represent the respective x direction (transverse direction) and y direction (vertical direction) averages of $P(i,j)$, and $\sigma x$ and $\sigma y$ represent the standard deviations of the same.

$$\text{correlation} = \frac{\sum_i \sum_j ij P_\delta(i, j) - \mu_x \mu_y}{\sigma_x \sigma_y} \qquad \text{[Formula 3]}$$

(4) Entropy

Entropy generally indicates the degree in which the uncertainty of information has decreased (stability), and is greater to the extent that $P(i,j)$ is uniformly allotted. Entropy has a quality opposite to that of the above (2) uniformity of texture. The distortion of the pattern image can be indicated by the entropy, since the distortion of the pattern image can be indicated by the uniformity of texture. Note that the entropy can be calculated using the formula below.

$$\text{entropy} = -\sum_i \sum_j P_\delta(i, j) \log P_\delta(i, j) \qquad \text{[Formula 4]}$$

Note that each index (1) to (4) described above may be used individually or in combination to calculate the image feature value. Moreover, a number of differing $\delta$ may be set in accordance with the shape of the projected light pattern or the region that is the object of image processing, with each of the resulting gray level co-occurrence matrices $P_\delta(i,j)$ used to calculate each index (1) to (4) described above. The indexes are then used in combination to obtain the image feature value.

Figure 11:
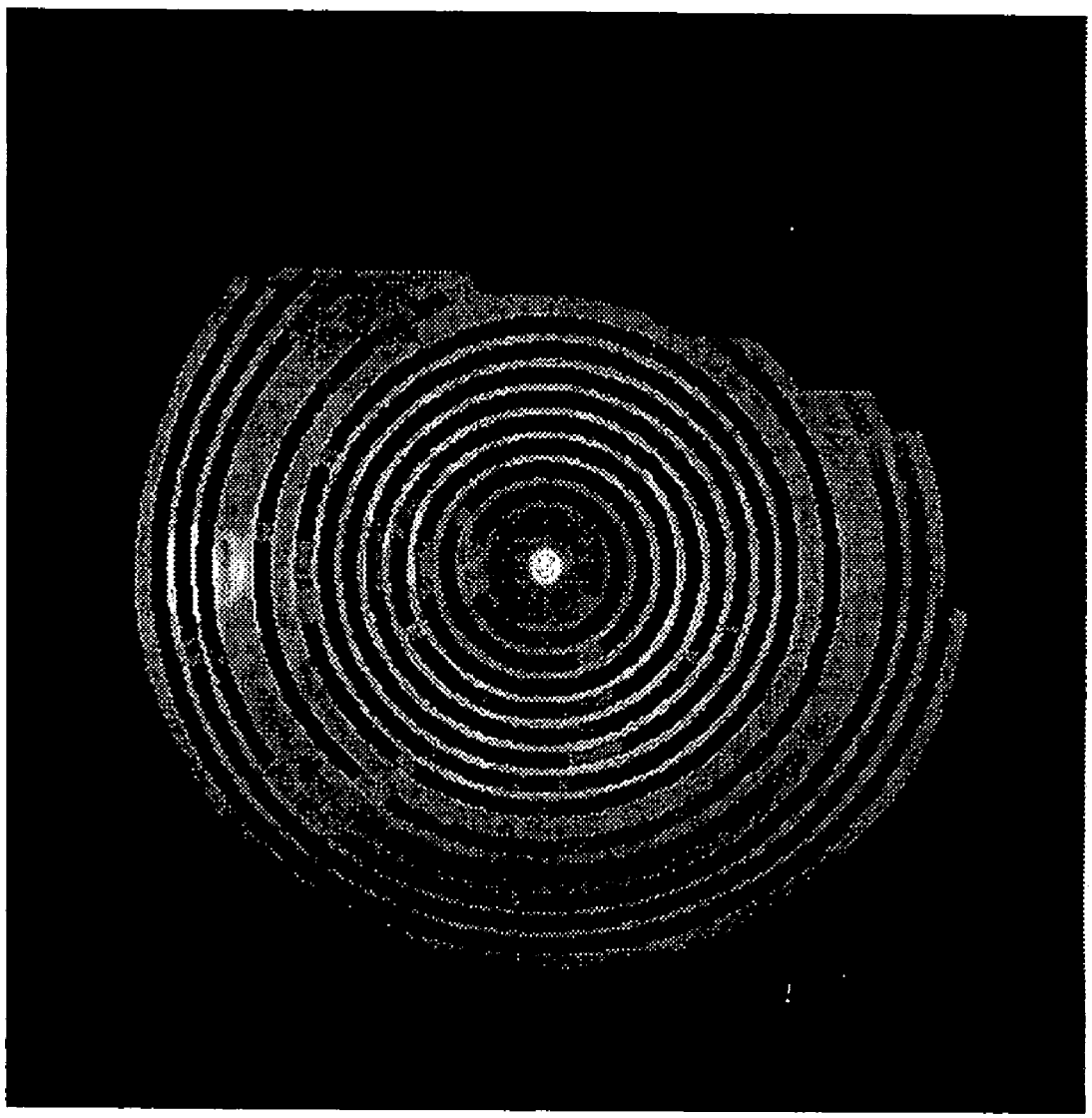
FIG. 11 is a view showing the amount of change in the image feature value calculated for the image shown in FIG. 10 when the image shown in FIG. 9 is set as a reference image.

FIG. 9 shows an image photographed immediately after the eyelid opens (at t=0 seconds), and FIG. 10 shows an image photographed two seconds after the eyelid opens (at t=2 seconds). FIG. 11 displays the amount of change in the image feature value, calculated for the image shown in FIG. 10, for each region that is an object of image processing when the image shown in FIG. 9 is set as a reference image. Note that in FIG. 11 entropy calculated with the gray level co-occurrence matrix $P_\delta(i,j)$ is used as the image feature value.

As is clear from FIG. 9, the reflection image (the ring pattern) reflected from the cornea surface immediately after the eyelid opens can be clearly recognized, and the lacrimal layer is very stable. On the other hand, as is clear from FIG. 10, the reflection image (the ring pattern) reflected from the cornea surface two seconds after the eyelid opens is blurred, in particular a disturbance in the region to the left of the center of the cornea is prominent. Thus, as shown in FIG. 11, the amount of change in the image feature value is also great in the region to the left of the center of the cornea. As is evident from the above explanation, when the distortion of the reflection image (the ring pattern) is great, the amount of change in the image feature value is also great, thus the distortion of the reflection image (the ring pattern) can be quantitatively evaluated.

Proceeding to step S16, the controller (12) reads from memory (10) one comparison image (at elapsed time t=1, . . . 10 seconds) for comparison with the reference image. More specifically, comparison images are read in the order that they are photographed. When a comparison image is read, the processing of steps S12 and S14 is performed on that comparison image (step S18). Thus the image feature values are calculated for the comparison images.

In step S20, the controller (12) calculates the difference between the image feature values of the corresponding regions of the reference image and of the comparison image.

Proceeding to step S22, the controller (12) determines for all of the regions whether the difference in image feature values exceeds a threshold value. Note that it has already been explained that the threshold value can be changed with the input device (13).

When the amount of change of the image feature value in any region exceeds the threshold value (YES in step S22), the controller (12) determines that a dry spot has occurred on the cornea surface (more specifically, that a dry eye state has been reached), and proceeds to step S26. In step S26 the controller (12) calculates the time until a dry spot occurs using the number of comparison images that have been read up to the threshold point, stores this time in the memory (10) as the breakup time, and finishes the image analysis processing. Accordingly, in the case in which four comparison images have been read before reaching step S26, the breakup time is $4 \times t_i$ ($t_i$=interval between photographs). Also, when the breakup time is calculated, image analysis processing is not performed for the subsequent photographed images, thus the measurement result is quickly displayed on the display device (09).

When the amount of change in the image feature values for all of the regions do not exceed the threshold value, (NO in step S22), the controller (12) proceeds to step S24. When the controller (12) proceeds to step S24, it determines whether the image feature values for all of the images have been calculated. When the image feature values for all of the images have been calculated (YES in step S24), the controller (12) ends processing without any further action. In this case, a dry eye state has not been observed. On the other hand, when the image feature values have not been calculated for all of the images (NO in step S24), the controller (12) returns to step S16 and repeats the processing from step S16 onward. In this manner, comparison images are read in order, the image feature values are calculated, and the state (dry eye state or not) of the lacrimal layer is judged.

Returning to FIG. 5, when image analysis processing in finished, the controller (11) displays the result of image analysis processing on the display device (09) (S07). In the present embodiment, the photographed images (FIGS. 9 and 10), the image feature values calculated for those images (FIGS. 11 and 12), and the breakup times obtained through image analysis processing are displayed.

As is clear from the above explanation, in the ophthalmologic apparatus of the present embodiment, all of the image data photographed by the CCD camera (08) is set as the information source, and the amount of change in the image feature values between the reference image (elapsed time t=0 seconds) and the comparison images is calculated (elapsed time t=1 to 10). More specifically, the present embodiment utilizes information concerning locations on the reflection image of the ring pattern projected onto the cornea that have blurred or merged with an adjacent location due to disruption of the lacrimal layer on the cornea surface. This information is used to calculate the degree of change (degree of change in the lacrimal layer) between the reference image and the comparison images. In this manner the state of the lacrimal layer can be evaluated with favorable precision.

However, in conventional corneal topographers, locations on the reflection image of the ring pattern projected onto the cornea, in which the reflection image of the ring pattern has blurred or adjacent pairs have merged due to disruption of the lacrimal layer on the cornea surface, are normally treated as defects in measurement, and the value of the location is interpolated from values on the periphery of the location (more specifically, information concerning the defects in measurement have not been used). In contrast the present embodiment has ventured to utilize the information concerning locations arising from the aforementioned defects in measurement that have not be used in the past. In this manner, the present embodiment measures the change over time in the lacrimal layer covering the cornea, with favorable precision.

Detailed explanations have been given above of several favorable embodiments of the present invention, however, these are merely examples, and the present embodiment can be changed in various ways and implemented with an improved configuration corresponding to the knowledge of a person skilled in the art.

For example, the projection pattern projected onto the cornea surface is not limited to concentric circles but may be set to a desired shape or pattern. Note that preferably the projection pattern is projected uniformly onto the entire cornea surface without uneven distribution in order to uniformly evaluate the entire cornea surface.

Also, the evaluation regions set in the images (regions for which image feature values are calculated) can be determined as appropriate in accordance with the projection pattern. The image feature values, which are indexes for indicating the distortion of the reflection image, can also be calculated using various methods, and the methods are not limited to those described in the configuration of the above embodiments.

For example, in the above embodiments, indexes (contrast, uniformity of texture, gray scale correlation, entropy) calculated using a gray level co-occurrence matrix are set as the image feature values, however, the image feature values can be calculated using fractal dimensions (an index indicating complexity) of the photographed images. Additionally, the image feature values can be calculated using a density histogram. Furthermore, the image feature values can be calculated by combining some of the above indexes (contrast, uniformity of texture, gray scale correlation, entropy, fractal dimension, density histogram), which are calculated using a gray level co-occurrence matrix.

Moreover the photographed images may be binarized into pixels with a high density value (the portion that reflects the light pattern) and into pixels with a low density value (the portion that does not reflect the light pattern). Then the pattern structured by the high density values may be thinned (by, for example, extracting the center lines), and the image feature values may be calculated on the basis of the shape of the thinned pattern. Also, when the change in the state of the lacrimal layer is extreme, the pattern is interrupted. Thus the number of interrupted points in the thinned pattern can also be set as the image feature value. Furthermore, points of light may be projected onto locations on the cornea surface, and the image feature value is calculated from the level of change in the coordinates of the reflection image.

In addition, the number of images of the reflection pattern from the cornea surface and the interval at which they are photographed can have various settings. For example, it can be determined that five to ten images are photographed during the maximum period that the eyelid is open. Also, the time intervals between photographs do not necessarily have to be equal.

In the above embodiments, the alignment of the optical system to the eye to be examined is performed manually, however, the alignment of the optical system may also be performed automatically.

Note that the technical elements disclosed in the present specification or drawings have technical utility separately or in all types of conjunctions and are not limited to the conjunctions set forth in the claims at the time of filing. Moreover, the art disclosed in the present specification or drawings achieve a plurality of objects simultaneously, and have technical utility by achieving one of those objects.

The invention claimed is:

1. An ophthalmologic apparatus for measuring the state of a lacrimal layer formed on a cornea surface of an eye to be examined, comprising:
    an optical projection system for projecting light of a ring-shaped pattern onto the cornea surface;
    an imaging device for photographing a ring-shaped pattern reflection image of the projected light from the cornea surface; and an operating unit for calculating the degree of distortion of the ring-shaped pattern reflection image on the basis of the density value distribution of the image photographed by the imaging device without calculating a cornea shape, wherein the operating unit further determines based only upon the calculated degree of distortion of the ring-shaped pattern reflection image whether the lacrimal layer reaches a state of dryness or not.

2. The ophthalmologic apparatus according to claim 1, wherein the operating unit:

(1) causes the imaging device to successively photograph reflection images from the cornea surface at specified intervals of time, and calculates the degree of distortion for each photographed image; and (2) sets one of the photographed images as a reference image, and determines that the lacrimal layer is in a specified state when the amount of change in the degree of distortion for the reference image exceeds a threshold value.

3. The ophthalmologic apparatus according to claim 2, further comprising an input device for inputting a change in the threshold value, the input device being designed to be operated by a person.

4. The ophthalmologic apparatus according to claim 2, wherein:

a plurality of regions are set in the images photographed by the imaging device; and the operating unit calculates the degree of distortion for each set region, and determines whether the state of the lacrimal layer has reached a specified state on the basis of the amount of change in the degree of distortion calculated for each set region.

5. The ophthalmologic apparatus according to claim 2, wherein the operating unit sets the first image photographed by the imaging device as a reference image, and determines whether the lacrimal layer has reached a specified state while calculating the amount of change in the degree of distortion for each of the images in the order of photographing.

6. The ophthalmologic apparatus according to claim 5, wherein the operating unit does not perform evaluation on images photographed subsequent to the image for which it is determined that the lacrimal layer has reached a specified state.

7. The ophthalmologic apparatus according to claim 1, wherein the operating unit calculates the degree of distortion of the reflection image from the relationship of the density values among pixels having a specified positional relationship in the photographed image.

8. The ophthalmologic apparatus according to claim 7, wherein the specified positional relationship is set in accordance with the pattern of light projected onto the cornea surface by the optical projection system.

9. The ophthalmologic apparatus according to claim 1, wherein the operating unit calculates a gray level co-occurrence matrix on the basis of the density value distribution of the photographed image, and calculates the degree of distortion from the calculated gray level co-occurrence matrix.

10. The ophthalmologic apparatus according to claim 3, wherein:

a plurality of regions are set in the images photographed by the imaging device; and the operating unit calculates the degree of distortion for each set region, and determines whether the state of the lacrimal layer has reached a specified state on the basis of the amount of change in the degree of distortion calculated for each set region.

11. The ophthalmologic apparatus according to claim 2, wherein the operating unit calculates the degree of distortion of the reflection image from the relationship of the density values among pixels having a specified positional relationship in the photographed image.

12. The ophthalmologic apparatus according to claim 11, wherein the specified positional relationship is set in accordance with the pattern of light projected onto the cornea surface by the optical projection system.

13. The ophthalmologic apparatus according to claim 4, wherein the operating unit calculates the degree of distortion of the reflection image from the relationship of the density values among pixels having a specified positional relationship in the photographed image.

14. The ophthalmologic apparatus according to claim 13, wherein the specified positional relationship is set in accordance with the pattern of light projected onto the cornea surface by the optical projection system.

15. The ophthalmologic apparatus according to claim 2, wherein the operating unit calculates a gray level co-occurrence matrix on the basis of the density value distribution of the photographed image, and calculates the degree of distortion from the calculated gray level co-occurrence matrix.

16. The ophthalmologic apparatus according to claim 13, wherein the operating unit calculates a gray level co-occurrence matrix on the basis of the density value distribution of the photographed image, and calculates the degree of distortion from the calculated gray level co-occurrence matrix.

17. An ophthalmologic apparatus for measuring the state of a lacrimal layer formed on a cornea surface of an eye to be examined, comprising:

an optical projection system for projecting a pattern of light and dark regions onto the cornea surface;

an imaging device for capturing an image of the cornea surface and the pattern projected on the cornea surface; and an operating unit for calculating a degree of distortion of the pattern of light and dark regions in the image based on a density value distribution of the captured image.

* * * * *